United States Patent
Shen et al.

(10) Patent No.: US 10,963,713 B2
(45) Date of Patent: Mar. 30, 2021

(54) ELECTRONIC DEVICE AND BIOLOGICAL MONITORING METHOD USING THE SAME

(71) Applicant: Wistron Corporation, New Taipei (TW)

(72) Inventors: Chih-Teng Shen, New Taipei (TW); Cheng-Wei Chang, New Taipei (TW)

(73) Assignee: Wistron Corporation, New Taipei (TW)

(*) Notice: Subject to any disclaimer, the term of this patent is extended or adjusted under 35 U.S.C. 154(b) by 174 days.

(21) Appl. No.: 16/158,289

(22) Filed: Oct. 11, 2018

(65) Prior Publication Data

US 2020/0012874 A1   Jan. 9, 2020

(30) Foreign Application Priority Data

Jul. 6, 2018   (TW) ................... 107123389

(51) Int. Cl.
| | |
|---|---|
| G06K 9/00 | (2006.01) |
| A61B 5/024 | (2006.01) |
| A61B 5/00 | (2006.01) |
| G01S 13/86 | (2006.01) |
| G01S 13/88 | (2006.01) |

(52) U.S. Cl.
CPC ...... *G06K 9/00885* (2013.01); *A61B 5/02438* (2013.01); *A61B 5/6898* (2013.01); *G01S 13/86* (2013.01); *G01S 13/88* (2013.01); *G06K 2009/00939* (2013.01)

(58) Field of Classification Search
CPC ...... G06K 9/00885; G06K 2009/00939; G01S 13/86; G01S 13/88; A61B 5/02438; A61B 5/6898; A61B 5/0507
USPC ........................................ 342/60, 61
See application file for complete search history.

(56) References Cited

U.S. PATENT DOCUMENTS

| | | | |
|---|---|---|---|
| 8,615,290 B2 | 12/2013 | Lin | |
| 2015/0257706 A1 | 9/2015 | Liang | |
| 2016/0048672 A1* | 2/2016 | Lux | H04W 12/0605 340/5.82 |
| 2018/0020917 A1* | 1/2018 | Lin | G06K 9/00885 600/300 |
| 2018/0353086 A1* | 12/2018 | Turner | G01S 13/88 |

FOREIGN PATENT DOCUMENTS

| | | |
|---|---|---|
| CN | 106805940 A | 6/2017 |
| CN | 107623669 A | 1/2018 |
| TW | 201802718 A | 1/2018 |

* cited by examiner

*Primary Examiner* — Erin F Heard
*Assistant Examiner* — Michael W Justice
(74) *Attorney, Agent, or Firm* — Winston Hsu

(57) ABSTRACT

An electronic device is disclosed. The electronic device includes a wireless module configured to emit a first radar signal and receive a second radar signal, which is the first radar signal reflected by a user; a gravity sensor configured to sense a status of the electronic device to generate a sensing result; and a control unit coupled to the wireless module and the gravity sensor, and configured to control the wireless module to emit the first radar signal when the sensing result conforms to an emitting condition and determine a physiological status of the user according to the second radar signal received by the wireless module.

13 Claims, 3 Drawing Sheets

ELECTRONIC DEVICE AND BIOLOGICAL MONITORING METHOD USING THE SAME

BACKGROUND OF THE INVENTION

1. Field of the Invention

The present invention relates to an electronic device and a biological monitoring method using the same, and more particularly, to an electronic device and biological monitoring method capable of monitoring physiological status of a user by sensing non-contact signals.

2. Description of the Prior Art

With the advancement and development of technology, many kinds of electronic devices have become indispensable to humans. Since these electronic devices often store personal information related to the user, a protection mechanism for the electronic device is necessary. For example, as well as password verification, biological information sensing such as fingerprint sensing and pupil sensing may also be utilized for fortifying and protecting the information security and reliability of the electronic device. The verification technique for a conventional electronic device often performs verification or recognition for the user via a "contact" method such as password verification, picture verification and fingerprint verification, when the user wants to login to the electronic device or read personal information. If, however, the password of the user is fraudulently utilized or cracked, or the user cannot easily execute the fingerprint recognition, this leads to safety concerns and inconvenience to the user as they cannot pass the identification verification or recognition. Therefore, an improvement to the conventional electronic device utilized for verifying identification of the user is necessary.

SUMMARY OF THE INVENTION

The present invention provides an electronic device and a biological monitoring method using the same to sense a physiological status of a user by non-contact radar signals so as to perform a biological monitoring function, and furthermore, to execute a function of biology recognition based on the sensed physiological status of the user, to thereby enhance the information security of the electronic device.

An embodiment of the present invention discloses an electronic device, comprising a wireless module configured to emit a first radar signal and receive a second radar signal, which is the first radar signal reflected by a user; a gravity sensor configured to sense a status of the electronic device to generate a sensing result; and a control unit coupled to the wireless module and the gravity sensor, and configured to control the wireless module to emit the first radar signal when the sensing result conforms to an emitting condition and determine a physiological status of the user according to the second radar signal received by the wireless module.

Another embodiment of the present invention discloses a biological monitoring method for an electronic device, comprising emitting a first radar signal when a status of the electronic device conforms to a emitting condition; receiving a second radar signal, which is the first radar signal reflected by a user; and determining a physiological status of the user according to the received second radar signal.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
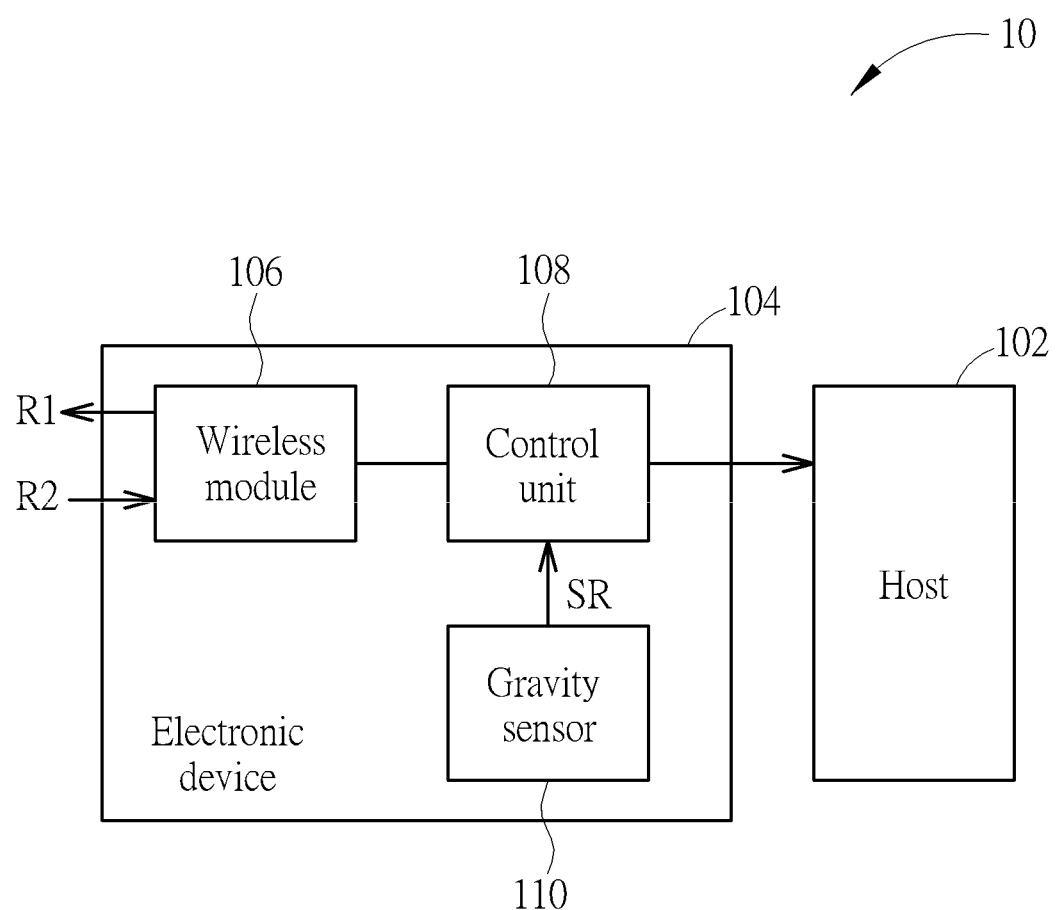
FIG. 1 is a schematic diagram of an electronic system according to an embodiment of the present invention.

Please refer to FIG. 1, which is a schematic diagram of an electronic system 10 according to an embodiment of the present invention. The electronic system 10 includes a host 102 and an electronic device 104. The host 102 may be an electronic device with an embedded controller (EC) or a microcontroller: for example, a personal computer, a desktop or a laptop. The electronic device 104 is coupled to the host 102, which includes a wireless module 106, a control unit 108 and a gravity sensor 110. The wireless module 106 is configured to emit a first radar signal R1 and receive a second radar signal R2, which is the first radar signal R1 reflected by a user. The gravity sensor 110 is configured to sense a status of the electronic device 104 to generate a sensing result SR. The control unit 108 is configured to control the wireless module 106 to emit the first radar signal R1 when it is determined that the sensing result SR of the gravity sensor 110 conforms to an emitting condition, and determine a physiological status of the user according to the second radar signal R2 received by the wireless module 106. For example, the gravity sensor 110 determines that the electronic device 104 conforms to the emitting condition only when the electronic device 104 is stationary, or only when the electronic device 104 is stationary for a predetermined time. In addition, the second radar signal R2 may include information of a heartbeat frequency or an electrocardiogram of the user. Therefore, when the sensing result SR shows that the status of the electronic device 104 satisfies the emitting condition, the control unit 108 actively activates the wireless module 106 to emit the first radar signal R1 and receives the second radar signal R2, which is the first radar signal R1 reflected by a user. Then, the control unit 108 determines the physiological status of the user according to the received second radar signal R2. In an embodiment, the electronic device 104 may be installed on an end of a laptop keyboard which is close to the user, so as to transmit and receive the radar signals. Therefore, it is not necessary for the user to contact the electronic device 104, meaning the electronic system 10 according to the embodiment of the present invention may actively detect the physiological status of the user and further perform an identification verification for the user according to the physiological status of the user.

In detail, the control unit 108 of the electronic device 104 according to the embodiment of the present invention may transmit the received second radar signal R2 to the host 102 with an analog-to-digital (ADC) conversion, so as to determine the physiological status of the user. In an embodiment, the first radar signal R1 and the second radar signal R2 may be radar signals having a frequency of 24 GHz. Therefore, after the control unit 108 receives the second radar signal R2 related to the physiological status of the user, the control unit 108 may perform ADC conversion for the second radar signal R2 in order to transmit it to the host 102, and the physiological status of the user is determined via an application interface of the host 102. The gravity sensor 110 is configured to detect a gravity environment of the electronic device 104. More specifically, the gravity sensor 110 may be an acceleration and kinetic energy sensing device for sensing variations of XYZ axes at a point where the electronic device 104 is located, so as to determine that the electronic device 104 is stationary or moving. For example, when the gravity sensor 110 senses that values of the acceleration and kinetic energy corresponding to the XYZ axes are all close to fixed values, the electronic device 104 is stationary, and the control unit 108 may determine whether to activate the wireless module 106 to emit the first radar signal R1 according to the status of the electronic device 104 detected by the gravity sensor 110. In other words, the control unit 108 determines whether to activate the wireless module 106 to emit the first radar signal R1 or not, according to whether the sensing result SR generated by the gravity sensor 110 conforms to the emitting condition or not, i.e. whether the electronic device 104 is stationary or moving. When the electronic device 104 is stationary, i.e. the sensing result SR conforms to the emitting condition, the control unit 108 accordingly controls the wireless module 106 to emit the first radar signal R1. In another embodiment, the emitting condition may be whether the electronic device 104 is stationary for the predetermined time or not. For example, when the gravity sensor 110 senses that the electronic device 104 is stationary for more than 30 seconds, i.e. when the sensing result SR conforms to the emitting condition, the control unit 108 determines that the sensing result SR conforms to the emitting condition and accordingly activates the wireless module 106 to emit the first radar signal R1.

In brief, under the circumstance of the electronic device 104 according to the embodiment of the present invention being stationary or being stationary for a period of time, the control unit 108 activates the wireless module 106 to emit the first radar signal R1 and receives the second radar signal R2 reflected by the user so as detect the heartbeat frequency or the electrocardiogram of the user. The host 102 determines a current body status of the user to thereby achieve the goal of biological monitoring. Notably, those skilled in the art may properly design the electronic device according to different system requirements not limited to those described above, and these also belong to the scope of the present invention.

According to different applications and design concepts, the electronic device 104 of the present invention may be implemented using all kinds of methods. In another embodiment, the control unit 108 transmits the received second radar signal R2, which is converted by ADC, to the host 102. Then, the host 102 may perform identification verification for the user according to the physiological status of the user. In detail, the host 102 may previously store, set or record a comparison status related to the user, such as a predetermined physiological status of the user or a physiological status related to the user, which is learned after the host 102 records the physiological status of the user multiple times. For example, the host 102 may record the heartbeat frequency or electrocardiogram of the user each time, and utilize these as the comparison status for verification. Therefore, when the host 102 receives the second radar signal R2 after the ADC conversion, the host 102 may perform the verification and confirmation based on the current received physiological status related to the user and the comparison status. When the comparison is identical or satisfied, the host 102 determines that the user passes the identification verification and allows the user to login to the host 102. When the host 102 determines that the physiological status of the user does not pass the verification, the host 102 does not allow the user to login. The host 102 may perform the identification verification according to varying characteristics of the heartbeat frequency or the electrocardiogram of the user, so as to enhance information security of the electronic device 104.

The electronic device 104 of the present invention determines whether the electronic device 104 satisfies the emitting condition or not (i.e. the electronic device is stationary or not) according to the sensing result SR of the gravity sensor 110, so as to activate the wireless module 106 to emit the non-contact radar sensing signal when the electronic device 104 conforms to the emitting condition, in order to obtain the physiological status of the user and monitor the physiological status of the user. In addition, the electronic device 104 may perform the identification verification by the sensed physiological status of the user, so as to allow the user to login to the host 102 when the sensed physiological status of the user conforms to the comparison status, and thereby enhance the information security of the electronic device 104.

Figure 2:
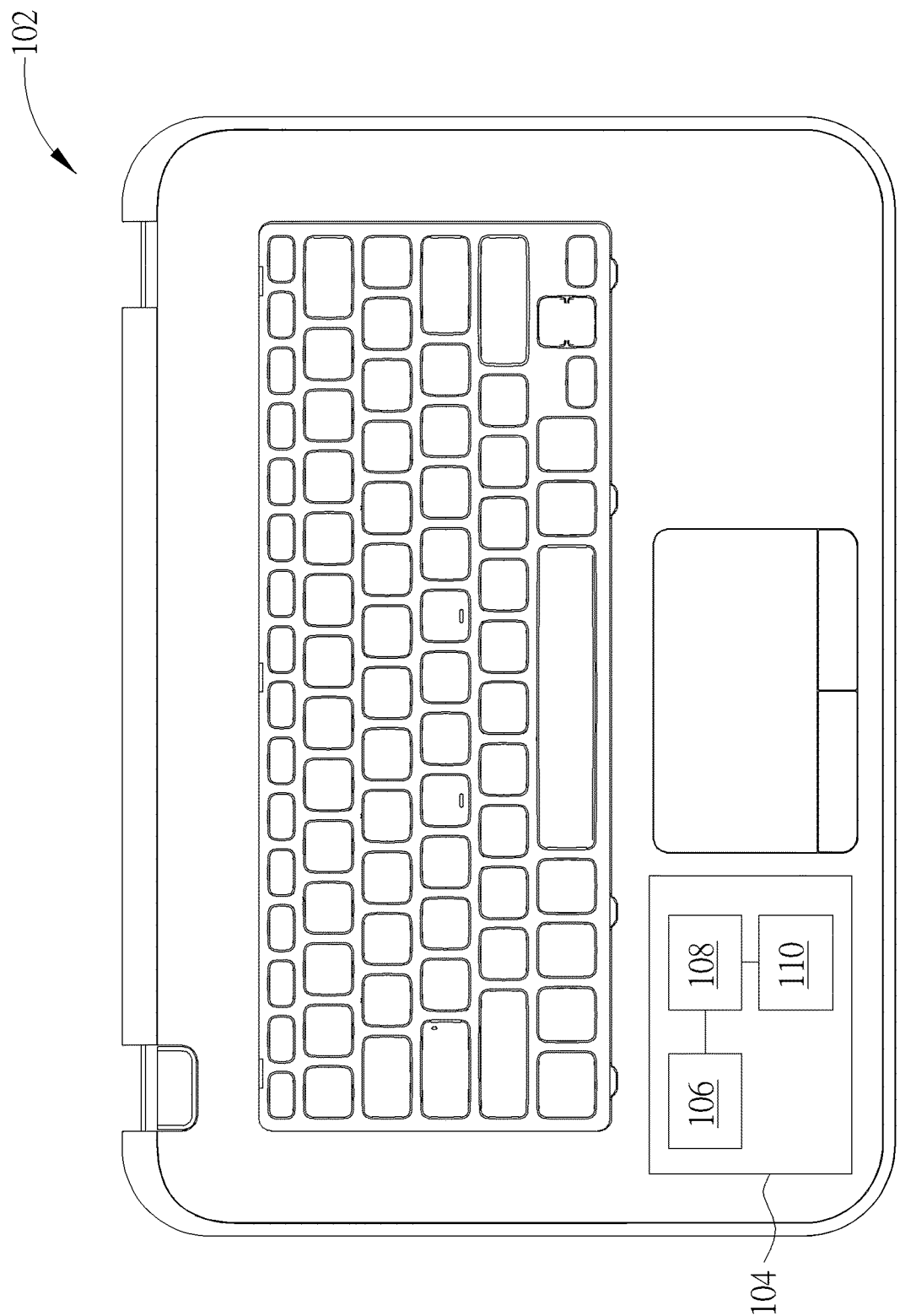
FIG. 2 is a schematic diagram of an implementation aspect of the electronic system according to an embodiment of the present invention.

According to different applications and design concepts, the electronic device 104 of the present invention may be implemented in all kinds of methods. Please refer to FIG. 2, which is a schematic diagram of an implementation aspect of the electronic system 10 according to an embodiment of the present invention. As shown in FIG. 2, when the electronic system 10 is applied on a laptop, the electronic device 104 may be installed in a place close to the user for emitting or receiving radar signals. It is not necessary for the user to directly contact the laptop to perform identification verification and for monitoring the physiological status of the user when the user operates the electronic system 10.

Figure 3:
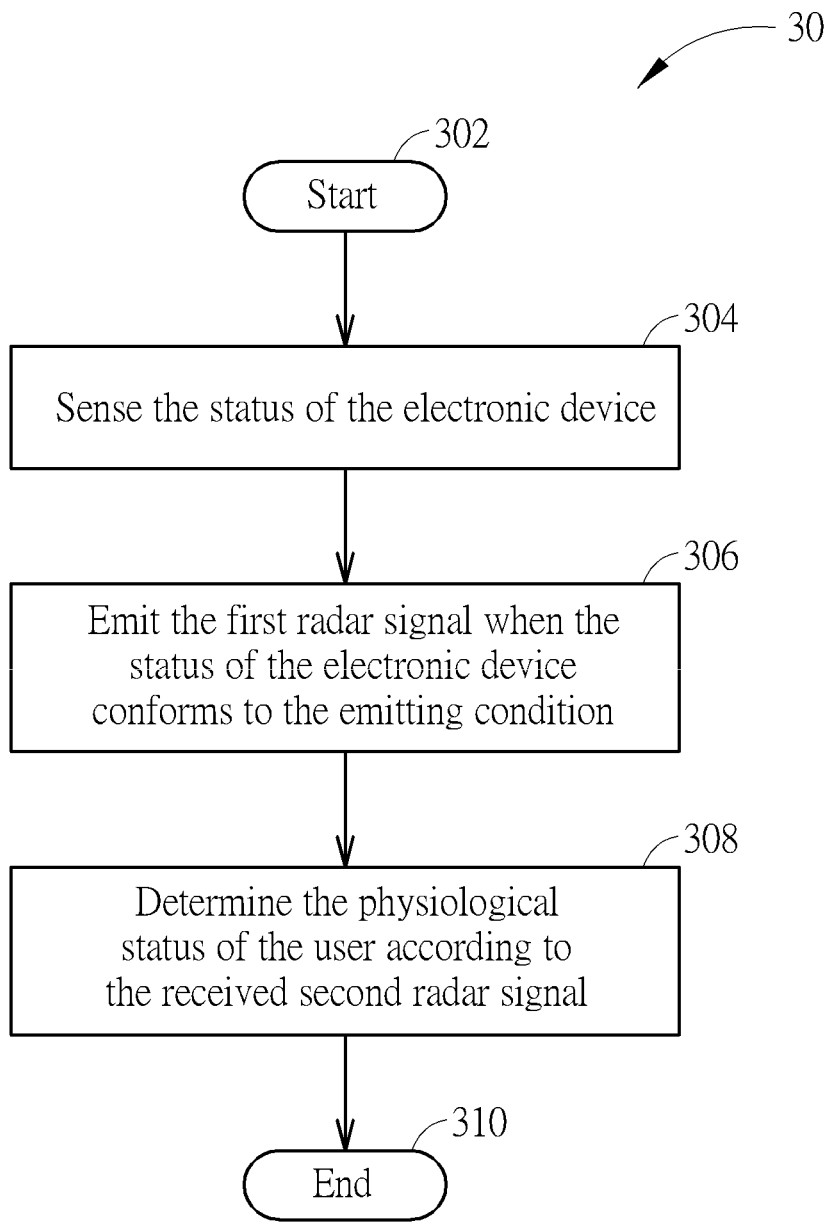
FIG. 3 is a schematic diagram of a biological monitoring method according to an embodiment of the present invention.

An operation method of the electronic device 104 may be a biological monitoring method 30, which is shown in FIG. 3. The biological monitoring method 30 includes the following steps:

Step 302: Start.

Step 304: Sense the status of the electronic device 104.

Step 306: Emit the first radar signal R1 when the status of the electronic device 104 conforms to the emitting condition.

Step 308: Determine the physiological status of the user according to the received second radar signal R2.

Step 310: End.

The operation of the biological monitoring method 30 can be known by referring to the embodiments of the electronic device 104 described above, and are therefore not repeated herein for brevity.

Notably, those skilled in the art may make modifications to properly design the electronic device based on different system requirements. For example, the frequency of the radar signal is not limited to be 24 GHz, the electronic device may be applied to medical devices for monitoring the physiological status of the user, or the electronic device may be applied on electronic devices different from personal computers or laptops for performing the identification verification. The embodiments mentioned above may all be adjusted according to requirements of the user, manufacturers or system settings, but are not limited thereto, and these adjustments also belong to the scope of the present invention.

In summary, the present invention provides an electronic device and a biological monitoring method using the same, which senses the physiological status of the user via non-contact radar signals, so as to execute a function of biological monitoring, and further perform a biological recognition function based on the sensed physiological status of the user and enhance the information security of the electronic device.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An electronic device, comprising:
a wireless module configured to emit a first radar signal and receive a second radar signal, which is the first radar signal reflected by a user;
a gravity sensor configured to sense a status of the electronic device to generate a sensing result; and
a controller coupled to the wireless module and the gravity sensor, and configured to control the wireless module to emit the first radar signal when the sensing result conforms to an emitting condition and determine a physiological status of the user according to the second radar signal received by the wireless module;
wherein the electronic device does not physically contact the user and the emitting condition is satisfied when the electronic device is stationary.

2. The electronic device of claim 1, wherein the physiological status of the user is related to a heartbeat frequency or an electrocardiogram of the user.

3. The electronic device of claim 1, wherein when a location variation of the electronic device sensed by the gravity sensor is fixed, the electronic device is determined as stationary.

4. The electronic device of claim 1, wherein the controller communicates the received second radar signal with a host system after digitalizing the received second radar signal via an analog-to-digital conversion to determine the physiological status of the user.

5. The electronic device of claim 4, wherein the host system performs an identification verification for the user according to the physiological status of the user.

6. The electronic device of claim 5, wherein when the physiological status of the user is identical to a comparison status, the host system determines that the user passes the identification verification and logs into the host system.

7. The electronic device of claim 6, wherein the comparison status is a predetermined physiological status or the physiological status related to the user and learned by the host system.

8. A biological monitoring method for an electronic device, comprising:
emitting a first radar signal when a status of the electronic device conforms to an emitting condition;
receiving a second radar signal, which is the first radar signal reflected by a user; and
determining a physiological status of the user according to the received second radar signal;
wherein the electronic device does not physically contact the user and the emitting condition is satisfied when the electronic device is stationary.

9. The biological monitoring method of claim 8, wherein the physiological status of the user is related to a heartbeat frequency or an electrocardiogram of the user.

10. The biological monitoring method of claim 8, wherein when a location variation of the electronic device sensed by the gravity sensor is fixed, the electronic device is determined as stationary.

11. The biological monitoring method of claim 8, further comprising:
performing an identification verification for the user according to the physiological status of the user.

12. The biological monitoring method of claim 11, further comprising:
when the physiological status of the user is identical to a comparison status, determining that the user passes the identification verification.

13. The biological monitoring method of claim 12, wherein comparison status is a predetermined physiological status or the physiological status related to the user and learned by a host system.

* * * * *